US00PP26998P2

(12) United States Plant Patent
Smith et al.

(10) Patent No.: US PP26,998 P2
(45) Date of Patent: Aug. 2, 2016

(54) ***DENDRANTHEMA* PLANT NAMED 'SNOWY IGLOO'**

(50) Latin Name: *Dendranthema×morifolium*
Varietal Denomination: Snowy Igloo

(71) Applicants: Mark A. Smith, Fort Myers, FL (US); Cornelis P. Vandenberg, Fort Myers, FL (US)

(72) Inventors: Mark A. Smith, Fort Myers, FL (US); Cornelis P. Vandenberg, Fort Myers, FL (US)

(73) Assignee: Aris Horticulture, Inc., Barberton, OH (US)

( * ) Notice: Subject to any disclaimer, the term of this patent is extended or adjusted under 35 U.S.C. 154(b) by 64 days.

(21) Appl. No.: 14/121,966

(22) Filed: Nov. 7, 2014

(51) Int. Cl.
*A01H 5/02* (2006.01)

(52) U.S. Cl.
USPC ..... Plt./288

(58) Field of Classification Search
USPC ..... Plt./288
See application file for complete search history.

*Primary Examiner* — Anne Grunberg
(74) *Attorney, Agent, or Firm* — C. A. Whealy

(57) ABSTRACT

A new and distinct cultivar of *Dendranthema* plant named 'Snowy Igloo', characterized by its upright, outwardly spreading and uniformly mounded to almost spherical plant habit; freely branching habit; dense and full plant form; uniform and freely flowering habit; decorative-type inflorescences; white-colored ray florets; natural season flowering occurs about September 13 to 23 in Pennsylvania; and good garden performance and winter hardiness.

2 Drawing Sheets

Botanical designation: *Dendranthema×morifolium.*
Cultivar denomination: 'SNOWY IGLOO'.

BACKGROUND OF THE INVENTION

The present invention relates to a new and distinct *Dendranthema* plant, botanically known as *Chrysanthemum×morifolium*, commercially grown as a perennial garden-type *Dendranthema* plant, and hereinafter referred to by the cultivar name 'Snowy Igloo'.

The new *Dendranthema* is the product of a planned breeding program conducted by the Inventors in Bogota, Colombia and Smoketown, Pa. The objective of the breeding program is to create new perennial garden-type *Dendranthema* plants having uniformly mounding plant habit, inflorescences with desirable inflorescence forms, attractive ray and disc floret shapes and colors, winter hardiness and good garden performance.

The new *Dendranthema* plant originated from a cross-pollination made by the Inventors in September, 2008, in Bogota, Colombia of *Chrysanthemum×morifolium* 'Frosty Yoigloo', disclosed in U.S. Plant Pat. No. 20,251, as the female, or seed, parent with a proprietary selection of *Chrysanthemum×morifolium* identified as code number H6643, not patented, as the male, or pollen, parent. The new *Dendranthema* plant was discovered and selected by the Inventors as a single flowering plant within the progeny of the stated cross-pollination in a controlled greenhouse environment in Smoketown, Pa. on Sep. 28, 2009.

Asexual reproduction of the new *Dendranthema* plant by vegetative cuttings was first conducted in a controlled greenhouse environment in Smoketown, Pa. in March, 2010 and such asexual propagation has shown that the unique features of this new *Dendranthema* plant are stable and reproduced true to type in successive generations.

SUMMARY OF THE INVENTION

Plants of the new *Dendranthema* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Snowy Igloo'. These characteristics in combination distinguish 'Snowy Igloo' as a new and distinct garden-type *Dendranthema* plant:

1. Upright, outwardly spreading and uniformly mounded to almost spherical plant habit.
2. Freely branching habit; dense and full plant form.
3. Uniform and freely flowering habit.
4. Decorative-type inflorescences.
5. White-colored ray florets.
6. Natural season flowering occurs about September 13 to 23 in Pennsylvania.
7. Good garden performance and winter hardiness.

In side-by-side comparisons, plants of the new *Dendranthema* differ from plants of the female parent, 'Frosty Yoigloo' primarily in plant size as plants of the new *Dendranthema* are larger than plants of 'Frosty Yoigloo'. In addition, under low night temperatures conditions, plants of the new *Dendranthema* and 'Frosty Yoigloo' differ in ray flower color as plants of 'Frosty Yoigloo' will "pink" whereas plants of the new *Dendranthema* will retain their white ray floret coloration.

In side-by-side comparisons, plants of the new *Dendranthema* differ primarily from plants of the male parent selection in the following characteristics:

1. Plants of the new *Dendranthema* are larger than plants of the male parent selection.
2. Plants of the new *Dendranthema* flower earlier than plants of the male parent selection.
3. Inflorescences of plants of the new *Dendranthema* have fewer disc florets than inflorescences of plants of the male parent selection.

4. Plants of the new *Dendranthema* and the male parent selection differ in ray floret color as plants of the male parent selection have golden yellow-colored ray florets.

Plants of the new *Dendranthema* can be compared to plants of *Chrysanthemum×morifolium* 'Icicle Igloo', disclosed in U.S. Plant patent application Ser. No. 13/998,708. In side-by-side comparisons, plants of the new *Dendranthema* differ from plants of 'Icicle Igloo' in the following characteristics:

1. Plants of the new *Dendranthema* are larger than plants of 'Icicle Igloo'.
2. Plants of the new *Dendranthema* have decorative-type inflorescences whereas plants of 'Icicle Igloo' have daisy-type inflorescences.
3. Plants of the new *Dendranthema* and 'Icicle Igloo' differ slightly in developing ray floret color.

BRIEF DESCRIPTION OF THE PHOTOGRAPHS

The accompanying photographs illustrate the overall appearance of the new *Dendranthema* showing the colors as true as it is reasonably possible to obtain in colored reproductions of this type. Colors in the photographs may differ slightly from the color values cited in the detailed botanical description which accurately describe the colors of the new *Dendranthema* plant.

The photograph on the first sheet comprises a side perspective view of a typical flowering plant of 'Snowy Igloo' grown in a container.

The photograph on the second sheet is a close-up view of a typical flowering plant of 'Snowy Igloo'.

DETAILED BOTANICAL DESCRIPTION

The aforementioned photographs and following observations and measurements describe plants grown during the early autumn in 25-cm containers in a polyethylene-covered greenhouse in Lancaster, Pa. and under cultural practices typical of commercial garden-type *Dendranthema* production. During the production of the plants, day temperatures averaged 26.7° C. and night temperatures ranged from 15.6° C. to 18.3° C. Plants were five months old when the photographs and description were taken. In the following description, color references are made to The Royal Horticultural Society Colour Chart, 2007 Edition, except where general terms of ordinary dictionary significance are used.

Botanical classification: *Chrysanthemum×morifolium* 'Snowy Igloo'.

Parentage:

*Female, or seed, parent.*—*Chrysanthemum×morifolium* 'Frosty Yoigloo', disclosed in U.S. Plant Pat. No. 20,251.

*Male, or pollen, parent.*—Proprietary selection of *Chrysanthemum×morifolium* identified as code number H6643, not patented.

Propagation:

*Type.*—Terminal vegetative cuttings.

*Time to produce a rooted young plant.*—About two weeks.

*Root description.*—Fine, fibrous; white in color.

*Rooting habit.*—Freely branching, dense.

Plant description:

*Plant and growth habit.*—Perennial garden-type *Dendranthema* plant with decorative-type inflorescences; upright, outwardly spreading and uniformly mounding to almost spherical plant habit; strong and vigorous growth habit.

*Branching habit.*—Freely branching habit, about primary lateral branches developing at potentially every node, each primary lateral with multiple secondary and tertiary branches; dense and full plant form; pinching is not required.

*Plant height.*—About 37 cm.

*Plant width.*—About 61.5 cm.

*Lateral branches.*—Length: About 31 cm. Diameter: About 3 mm. Internode length: About 1.5 cm. Strength: Strong. Texture: Pubescent, minute; longitudinally ridged. Color: Close to 146A.

*Leaves.*—Arrangement: Alternate, simple. Length: About 3.3 cm. Width: About 2.7 cm. Apex: Cuspidate. Base: Truncate. Margin: Palmately lobed, sinuses between lateral lobes mostly parallel to divergent. Texture, upper surface: Smooth, glabrous. Texture, lower surface: Pubescent, minute; veins prominent on lower surface. Venation pattern: Pinnate. Color: Developing and fully expanded leaves, upper surface: Close to N137A; venation, close to 137A. Developing and fully expanded leaves, lower surface: Close to 137B; venation, close to 146A to 146B. Petioles: Length: About 1.1 cm. Diameter: About 2 mm. Texture, upper surface: Smooth, glabrous. Texture, lower surface: Pubescent; minute. Color, upper surface: Close to N137A. Color, lower surface: Close to 137B.

Inflorescence description:

*Type and arrangement.*—Decorative-type inflorescence form with elongated oblong-shaped ray florets; disc and ray florets arranged acropetally on a capitulum; inflorescences face mostly upright to outwardly and held above and beyond the foliar plane on strong peduncles.

*Fragrance.*—None detected.

*Flowering response.*—Under natural season conditions, plants flower about September 13 to 23 in Pennsylvania.

*Postproduction longevity.*—Inflorescences maintain good color and substance for about three to six weeks on the plant depending on temperatures; inflorescences persistent.

*Quantity of inflorescences.*—Freely flowering habit with about five inflorescences developing per lateral branch.

*Inflorescence buds.*—Height: About 4 mm. Diameter: About 4.5 mm. Shape: Oblate to spherical. Color: Close to N137A.

*Inflorescence size.*—Diameter: About 2.6 cm. Depth (height): About 1.25 cm. Disc diameter: About 2 mm. Receptacle diameter: About 4 mm. Receptacle height: About 4 mm.

*Receptacle color.*—Close to 144A to 144B.

*Ray florets.*—Quantity and arrangement: About 132 ray florets develop per inflorescence and arranged in numerous whorls. Length: About 1.4 cm. Width: About 4 mm. Shape: Elongated oblong. Apex: Emarginate. Base: Attenuate and then fused into a short tube. Margin: Entire. Orientation: Initially upright, then arching outwardly. Texture, upper and lower surfaces: Smooth, glabrous; velvety; longitudinally ribbed. Color: When opening, upper surface: Close to 6D; at the base, close to 144A. When opening, lower surface: Close to 6D. Fully opened, upper surface: Close to NN155D; at the base, close to 144A; color does not change with development. Fully opened, lower surface: Close to NN155D; color does not fade with development.

*Disc florets*.—Quantity and arrangement: None to about twelve fused disc florets develop per inflorescence and massed at the center of the capitulum; inconspicuous. Length: About 4 mm. Diameter: About 1 mm. Shape: Tubular, elongated. Apex: Five-pointed. Texture, inner and outer surfaces: Smooth, glabrous. Color, mature: Apex: Close to 12A. Mid-section: Close to 144B to 144C. Base: Close to NN155D.

*Phyllaries*.—Quantity and arrangement: About 18 phyllaries develop per inflorescence and arranged in about two to three whorls. Length: About 5 mm. Width: About 2.5 mm. Shape: Lanceolate. Apex: Acute. Base: Truncate, fused. Margin: Entire; membraneous. Texture, upper surface: Smooth, glabrous. Texture, lower surface: Pubescent, minute. Color, upper and lower surfaces: Close to 137A.

*Peduncles*.—Length, terminal peduncle: About 2.4 cm. Length, fourth peduncle: About 3.6 cm. Diameter, terminal peduncle: About 1.5 mm. Angle: Mostly upright or curving upright. Strength: Strong, wiry. Texture: Pubescent; minute. Color: Close to 146A.

*Reproductive organs*.—Androecium (present on disc florets only): Stamen number: Five per floret. Filament length: About 4 mm. Filament color: Close to 150D. Anther length: Less than 1 mm. Anther shape: Narrowly oblong. Anther color: Close to 12A. Pollen amount: None observed. Gynoecium (present on ray and disc florets): Pistil length: About 4 mm. Stigma shape: Bi-parted. Stigma color: Close to 6A. Style length: About 3.5 mm. Style color: Close to 154D. Ovary color: Close to 144A.

*Seeds and fruits*.—Seed and fruit production has not been observed on plants of the new *Dendranthema*.

Disease & pest resistance: Resistance to pathogens and pests common to *Dendranthema* plants has not been observed on plants of the new *Dendranthema* grown under commercial production conditions.

Garden performance & temperature tolerance: Plants of the new *Dendranthema* have demonstrated excellent garden performance, are hardy to USDA Zone 5 and tolerate high temperatures about 37.8° C.

It is claimed:

1. A new and distinct *Dendranthema* plant named 'Snowy Igloo' as illustrated and described.

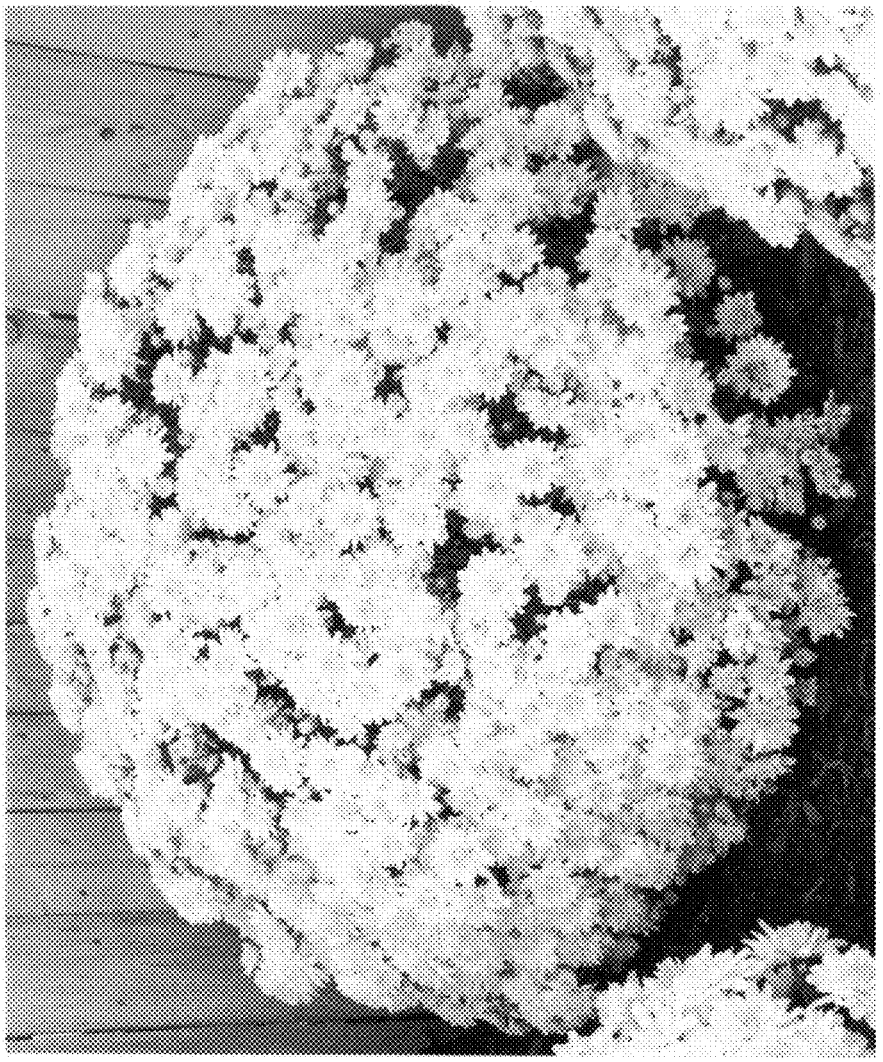

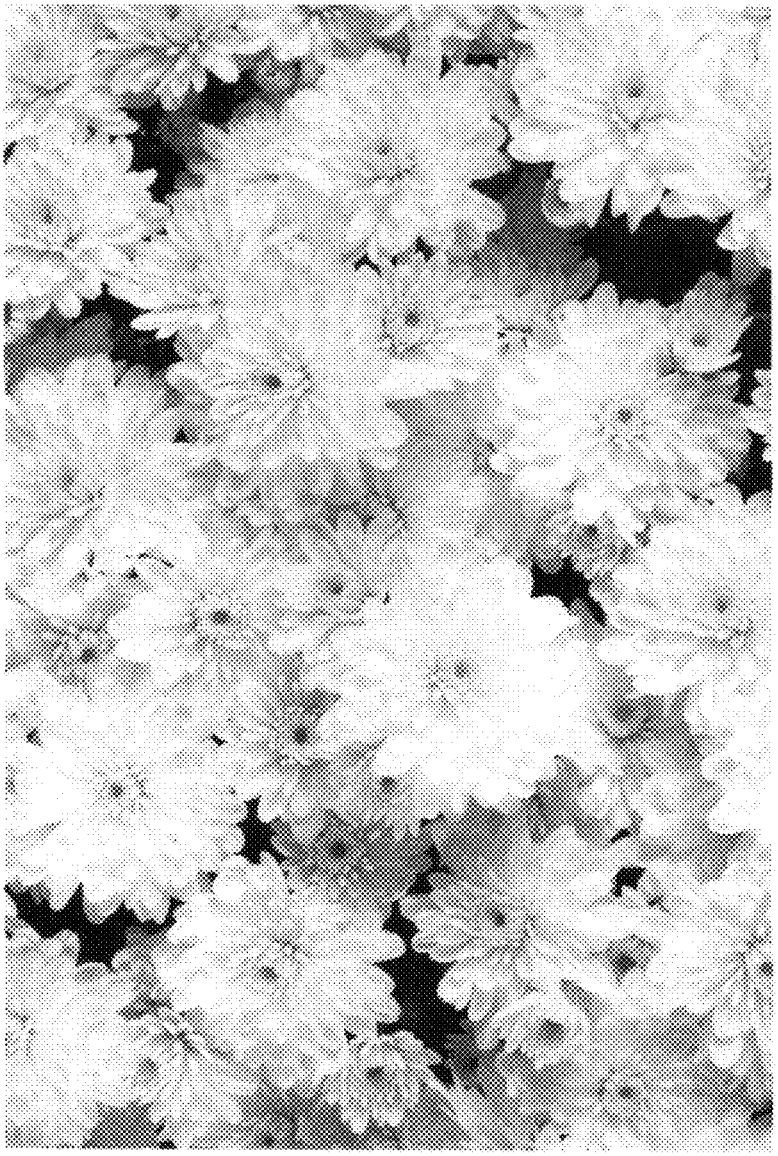

* * * * *